(12) United States Patent
Sen et al.

(10) Patent No.: US 6,418,081 B1
(45) Date of Patent: Jul. 9, 2002

(54) SYSTEM FOR DETECTION OF BURIED OBJECTS

(75) Inventors: Surajit Sen, Williamsville, NY (US); Michael J. Naughton, Norwood, MA (US)

(73) Assignee: The Research Foundation of State University of New York, Amherst, NY (US)

( * ) Notice: Subject to any disclaimer, the term of this patent is extended or adjusted under 35 U.S.C. 154(b) by 0 days.

(21) Appl. No.: 09/692,789

(22) Filed: Oct. 20, 2000

Related U.S. Application Data

(63) Continuation-in-part of application No. 09/247,499, filed on Feb. 10, 1999, now abandoned.
(60) Provisional application No. 60/074,187, filed on Feb. 10, 1998, and provisional application No. 60/217,959, filed on Jul. 13, 2000.

(51) Int. Cl.⁷ ............................. G01V 1/04; G01N 29/00
(52) U.S. Cl. ..................... 367/99; 181/101; 181/108; 181/112; 73/628
(58) Field of Search ........................... 367/99; 181/108, 181/112, 101; 73/594, 596, 628, 627

(56) References Cited

U.S. PATENT DOCUMENTS

| | | | |
|---|---|---|---|
| 4,016,486 A | 4/1977 | Pecori | 324/3 |
| 4,641,566 A | 2/1987 | Pomeroy | 89/1.13 |
| 5,357,063 A | 10/1994 | House et al. | 181/108 |
| 5,412,988 A | 5/1995 | Neff et al. | 73/517 R |
| 5,563,848 A | 10/1996 | Rogers et al. | 367/99 |
| 5,739,686 A | 4/1998 | Naughton et al. | 324/259 |
| 5,808,969 A | 9/1998 | Arnaud et al. | 367/103 |
| 5,923,166 A | 7/1999 | Naughton et al. | 324/244 |
| 5,925,822 A | 7/1999 | Naughton | 73/628 |
| 5,974,881 A | 11/1999 | Donskoy et al. | 73/579 |
| 6,055,214 A | * 4/2000 | Wilk | 367/99 |

OTHER PUBLICATIONS

Naughton et al., Detection of Non–Metallic Landmines Using Shock Impulses and Mems Sensors, Detection of Abandoned Land Mines, Oct. 12–14, 1998, Conference Publication No. 458, IEE 1998.

Sen, et al., Solitonlike Pulses In Perturbed and Driven Hertzian Chains and Their Possible Applications In Detecting Buried Impurities, Physical Review E, vol. 57, No. 2, Feb. 1998.

* cited by examiner

Primary Examiner—Ian J. Lobo
(74) Attorney, Agent, or Firm—Hodgson Russ LLP

(57) ABSTRACT

The present invention discloses a buried object detection system. The detection system has an acoustic emitter capable of generating a non-linear acoustic impulse or a continuous acoustic signal of variable amplitude and frequency. Sensors are deployed on an appropriate surface or surfaces of a granular medium, which are capable of detecting the backscattered and, if possible, forward scattered signals of the original impulse or wave from a buried inclusion or inclusions. The information received by the sensors may be transmitted to a computer for further manipulation and analysis.

16 Claims, 17 Drawing Sheets

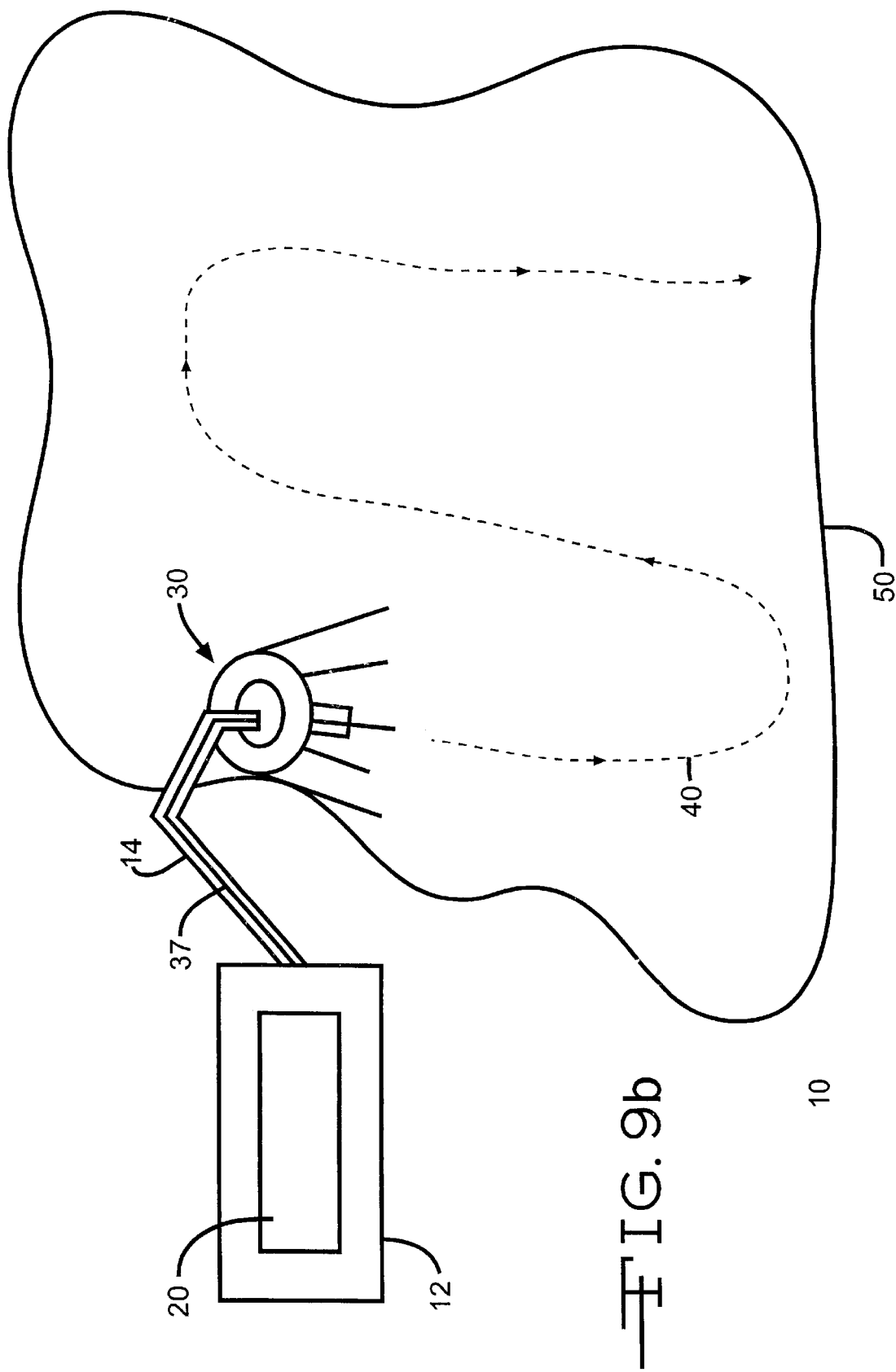

Piezoresistive Element

SYSTEM FOR DETECTION OF BURIED OBJECTS

This patent application is a continuation-in-part of U.S. patent application Ser. No. 09/247,499, filed Feb. 10, 1999, now abandoned, which claims priority to U.S. Provisional Patent Application Ser. No. 60/074,187, filed Feb. 10, 1998. This patent application also claims the benefit of U.S. Provisional Patent Application Ser. No. 60/217,959, filed Jul. 13, 2000.

This patent application was made under a Federal grant sponsored by the United States Army Corps of Engineers (Project #DACA-39-97-K0026.)

The present invention relates to detecting buried. inclusions, and, in particular, land mines with plastic casings. In its broader aspects it is relevant to detecting inclusions buried in granular media whose grains can be described by their elastic constants.

BACKGROUND

There are millions of unexploded and abandoned land mines. When abandoned land mines are triggered by unsuspecting people, equipment or livestock, they cause unexpected damage. People are often killed or permanently injured by such explosions.

Land mines are used in military conflicts to defend a mined field against an enemy. The mines are often quickly placed. Either poor or no records are made of the placement of the mines. After the conflict is over, the mines remain in place and are a deadly hazard to people, equipment and livestock. Mines that have a metal casing are readily detectable with customary mine sweepers. However, military technology now produces less expensive mines that have plastic or non-metallic casings. Mine sweepers cannot detect such mines. This has created an urgent need for a method and apparatus to detect plastic mines. Such a detection system would save many civilians from death and injury and also protect equipment and livestock.

In a more general sense, it is often desirable to detect buried objects in a granular medium. One often uses electromagnetic detection technologies to locate buried objects in optically opaque media. The success of detection technologies that are based upon electromagnetic waves is contingent upon the presence of materials in the buried objects that allow for the electromagnetic waves to pass through. Non-metallic objects are typically difficult to detect satisfactorily using electromagnetic waves.

An example of a non-metallic buried object is a land mine in a plastic casing, which we will refer to as a "plastic land mine." Plastic land mines contain a minimal amount of metal. The smallest amount of metal in a plastic land mine makes it detectable by conventional means based upon electromagnetic waves. Land mines are designed to avoid detection. Land mine manufacturers have therefore attempted to minimize and even eliminate metal in plastic land mines. The presently available land mines in plastic casings typically contain a very small amount of metal. Such small metal content makes them difficult to detect by conventional electromagnetic means because it is difficult to separate the backscattered electromagnetic signals received from a plastic land mine, from metal scrap and clutter that are inevitably present in the ground.

PRIOR ART

Arnaud, et al., U.S. Pat. No. 5,808,969 describes a process and device for detecting objects such as land mines using a plurality of acoustic transducers, working in the frequency range 10 Hz to 100 kHz. However, the process and device described in Arnaud were for continuous wave frequencies only, not for impulses, and the patent makes no mention of non-linear acoustics, solitons, or MEMS sensors.

Neff, et al., U.S. Pat. No. 5,412,988 describes an acceleration sensor with a microelectromechanical bender bar used in conjunction with a ferromagnetic core and a superconducting quantum interference device (SQUID). The primary detector in this scheme is the SQUID, which is stated to possess high sensitivity in a preferred frequency range of 1,000 to 10,000 Hz. The present invention does not require a ferromagnetic core or a SQUID sensor.

Other prior art of interest includes U.S. Pat. No. 5,563,848, A. J. Rogers and C. G. Don, titled Object Detector for Detecting Buried Objects and U.S. Pat. No. 5,357,063, L. J. House and D. B. Pape, titled Method and Apparatus for Acoustic Energy Identification of Objects Buried in Soil.

SUMMARY

The present invention solves the problem of detecting land mines with little or no metal. The present invention is capable of detecting buried objects or inclusions and of remotely imaging them whether or not there is metal in any of these objects. The detection process in the present invention is based upon newly discovered knowledge concerning (i) the soliton-like propagation of non-linear acoustic impulses in which the acoustic energy being sent through the granular medium suffers very little dispersion or spreading, and (ii) low-frequency continuous acoustic signals. The detection process in the present invention may be applied in granular media consisting of macroscopic elastic grains having a buried inclusion or inclusions. As a result, the invention provides a method and apparatus for locating buried inclusions by sensing the densities that differ from that of the medium itself. The invention also provides a probe that can reveal an image of what is buried in a granular bed without being sensitive to the metal content of the buried object.

The invention uses the following force law that describes the repulsion between two macroscopic elastic grains in contact:

$$F = na\delta^{n-1},$$

where n>2, as shown by H. Hertz in 1881 (Ref. H. Hertz, *J. reine u. angew. Math.* Vol. 92, p.156 (1881)), and "a" is a constant that depends upon the Young's modulus and the Poisson ratio of the materials of the grains in contact.

The present invention uses a soliton-like pulse. That pulse is a non-linear acoustic impulse. It is characterized by some pressure change of desired amplitude (typically less than 0.01 atmospheres) imparted to a surface of a granular bed across a time window of the order of a few micro-seconds or so. We have discovered that at some depth, z (z>10 d), where "d" is the average diameter of grains in the medium, from the surface of the three dimensional bed of granular beads in which the pulse has been initiated and in which the adjacent grains repel each other, the pulse can be. approximately described by the following functional form, $$\Phi_n(z) \approx A(Y,\sigma)\exp[-g(w,\rho,z)]\tan h(f_n(z)/2),$$

where A(Y, σ) is some amplitude of the non-linear acoustic pulse which depends upon the details of the generation of the acoustic pulse and upon the elastic constants characterizing the grains, and g(w, ρ, z) is some simple (usually linear)

function of "w", ρ and z, where "w" denotes the restitutional loss between the granular contacts as the grains load and unload during the propagation of a non-linear acoustic impulse and ρ denotes randomness in the size variation of the grains. The quantity z corresponds to the depth reached by the signal as measured from the surface of the bed.

Typically, these highly non-linear acoustic pulses travel with little dispersion. If one neglects this dispersion, then one may write, z≈ct, where "c" is the velocity of the non-linear acoustic pulse and hence relates the depth z to the time of travel t. The argument of the hyperbolic tangent function in $\Phi_n(z)$ above is, $$f_n(z) = \Sigma_{q=0}^{\infty} C_{2q+1}(n) z^{2q+1},$$

where the coefficients $C_{2q+1}$ (n) depend upon the magnitude of "n," which in turn relates to the geometric and material properties of the grains. See S. Sen and M. Manciu, *Discrete Hertzian Chains And Solitons,* Physica A, Vol. 268, pp 644–649, 1999. For our purposes, the quantity $\Phi_n(z)$ describes the relative displacement suffered by any grain, as a non-linear acoustic impulse passes through the grain. The pulse typically causes grain compressions in excess of one-millionth of the diameter of an average grain.

DRAWINGS

FIG. 1 is a graph showing the typical displacements of grains from their original equilibrium positions in a one-dimensional chain of granular beads as a soliton pulse passes through it. A typical grain in a three-dimensional granular bed exhibits very similar motion as a soliton-like pulse passes through the grain. The corresponding velocities and accelerations are given in FIGS. 2 and 3, respectively.

Figure 4:
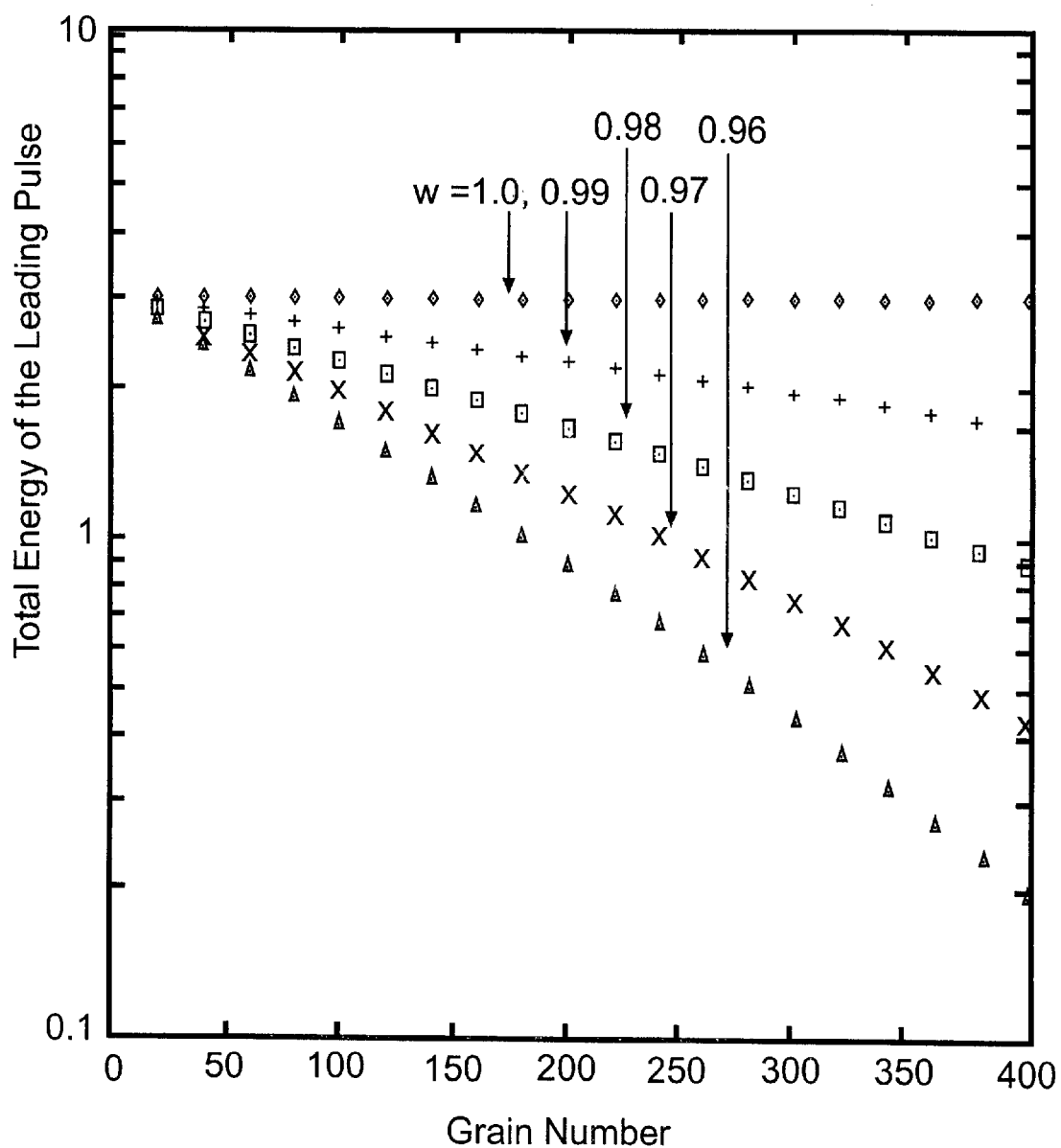

FIG. 4 is a graph showing the typical attenuation of the amplitude of the total energy associated with the signal in space and hence in time in a one-dimensional chain of granular beads when there are restitutional losses between the granular contacts. The restitutional loss can be generally defined as the 1−w, where force associated with unloading divided by force associated with loading between individual granular contacts is on average equal to w, where w is greater than zero and less than 1 in the presence of finite restitution. The results are also applicable for approximately analyzing the effects of restitutional loss in three-dimensional granular beds.

Figure 5:
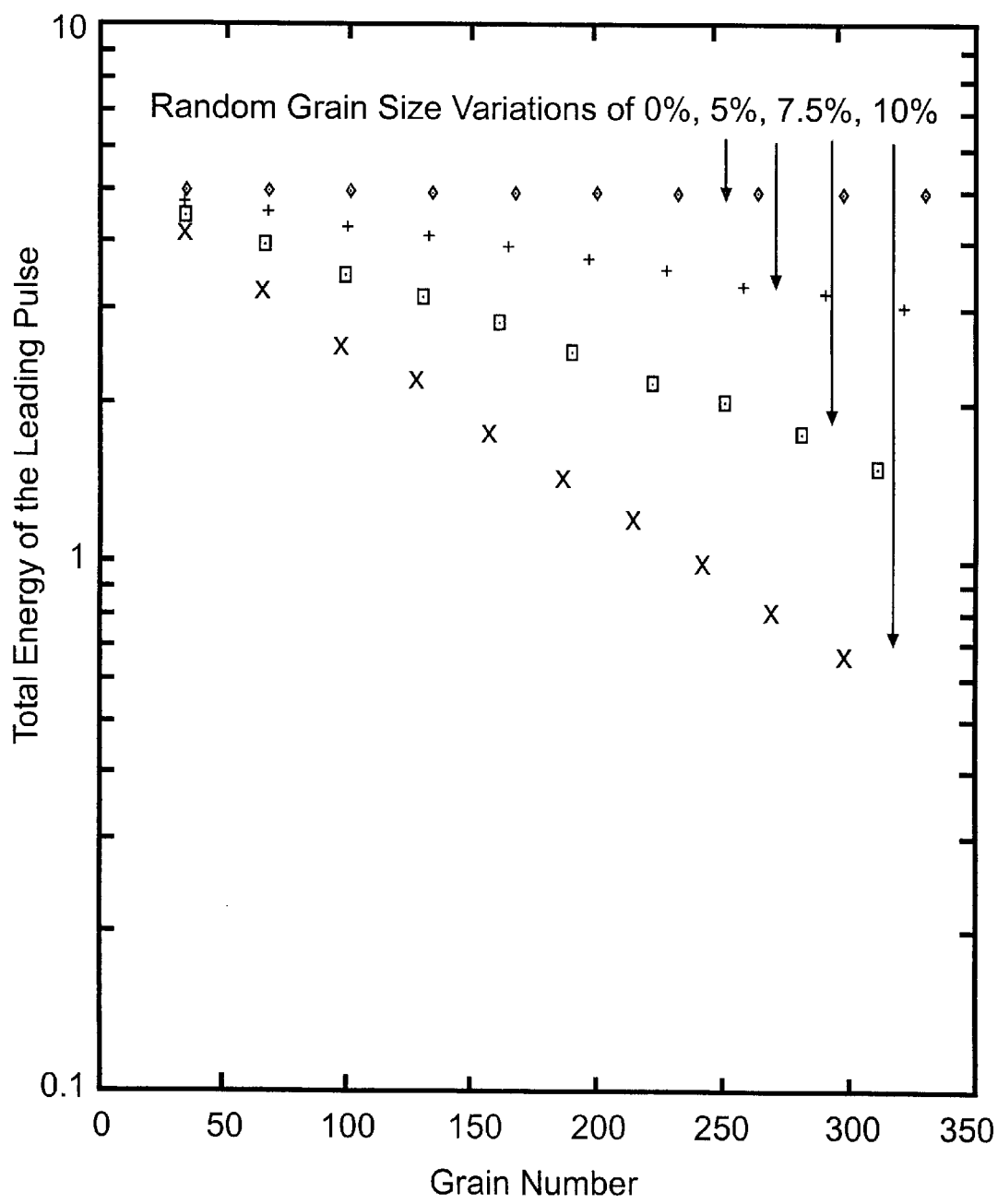

FIG. 5 is a graph showing the typical effects of randomness in grain sizes for various degrees of randomness on the amplitude of the total energy of the propagating wave in a one-dimensional chain of granular beads. The results are also applicable for approximately analyzing the effects of restitutional losses in three-dimensional granular beds in the presence of gravity.

Figure 6:
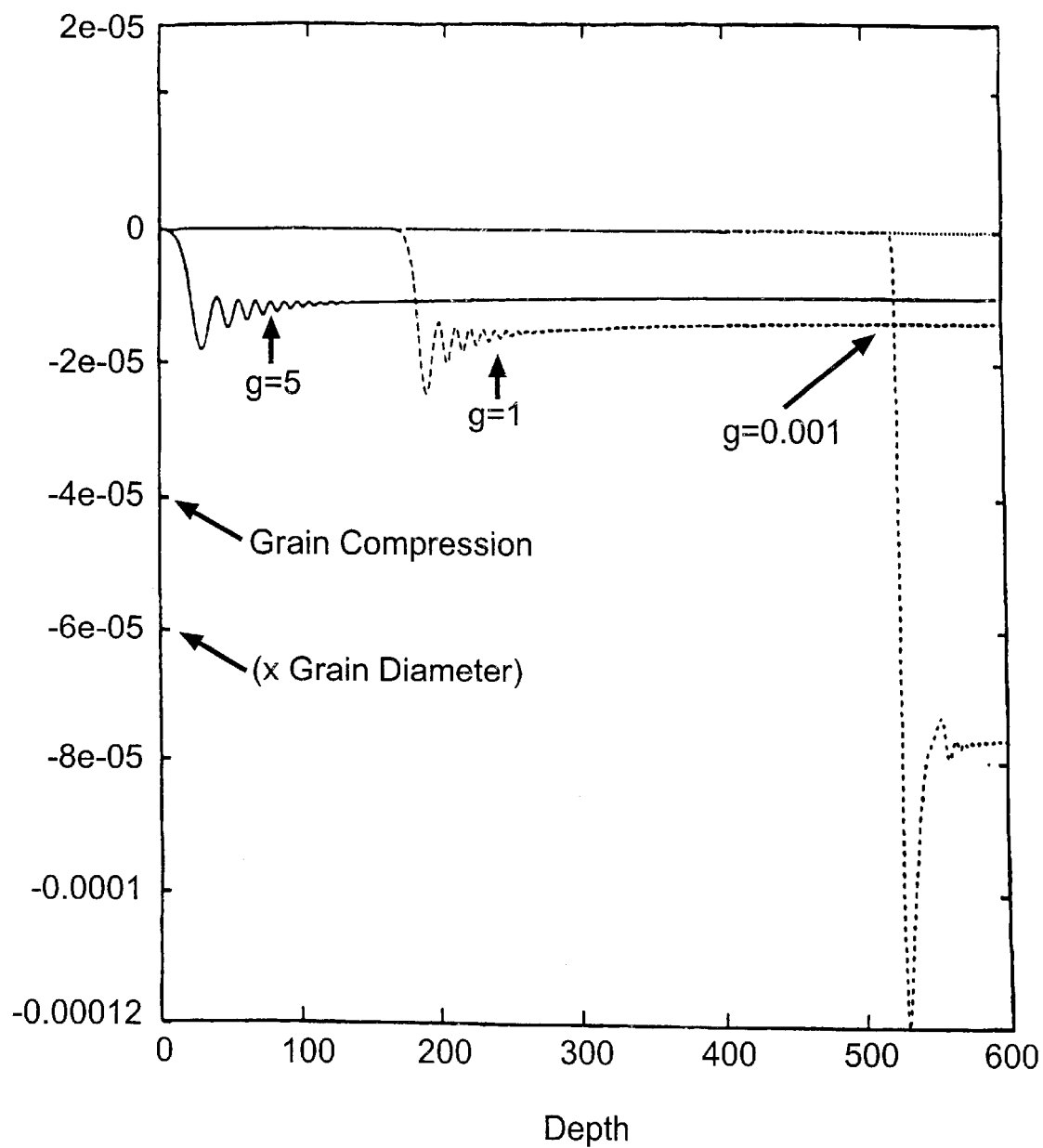

FIG. 6 is a graph showing an example of the dispersion of the pulse with increasing gravitational field for a soliton-like pulse traveling in a one-dimensional chain of granular beads. The results shown are representative of dispersion in three-dimensional granular beds also.

Figure 7:
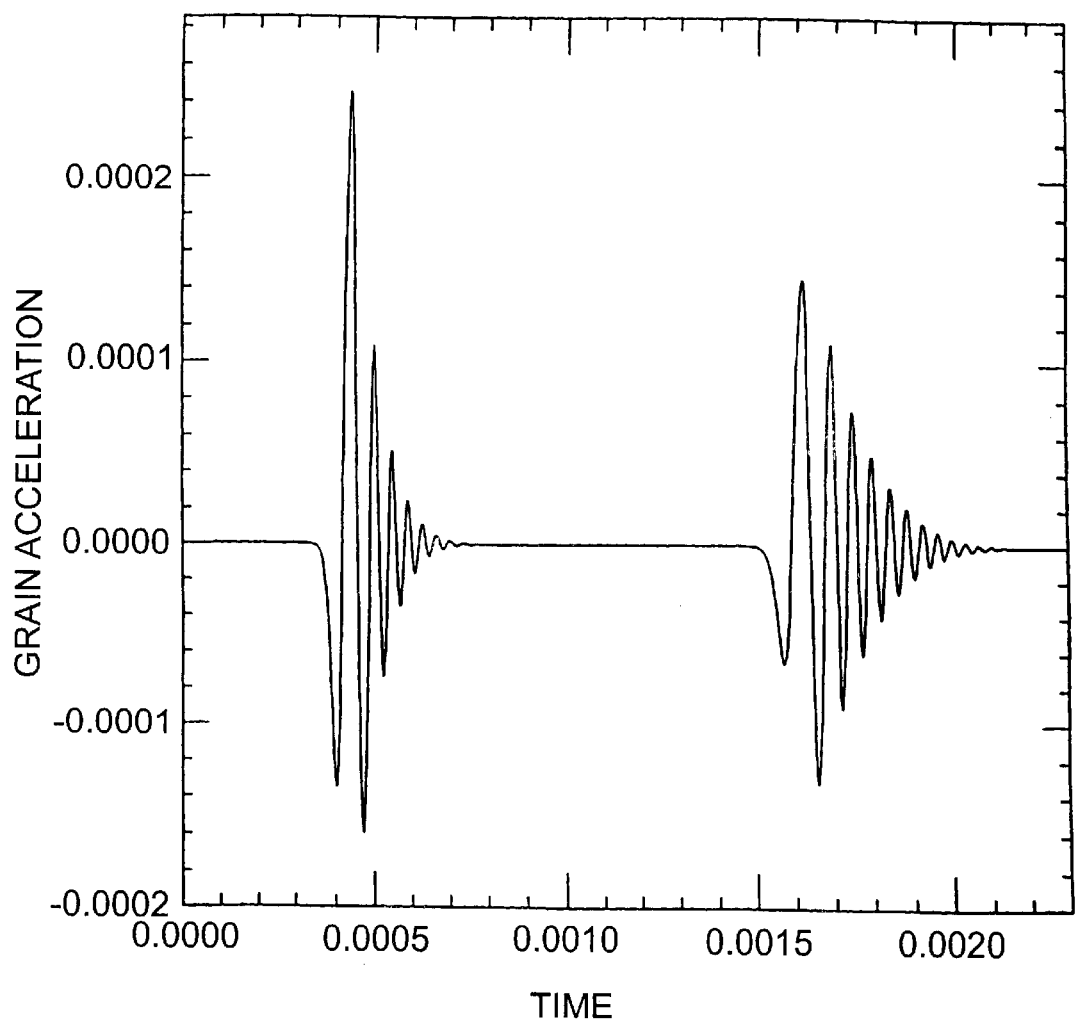

FIG. 7 is a graph showing the nature of the change in the shape of a soliton-like signal as it travels through a granular chain that is subjected to an applied field such as gravity as shown above. Acceleration of grains at different depths in a gravitationally loaded one-dimensional chain is shown.

Figure 8A:
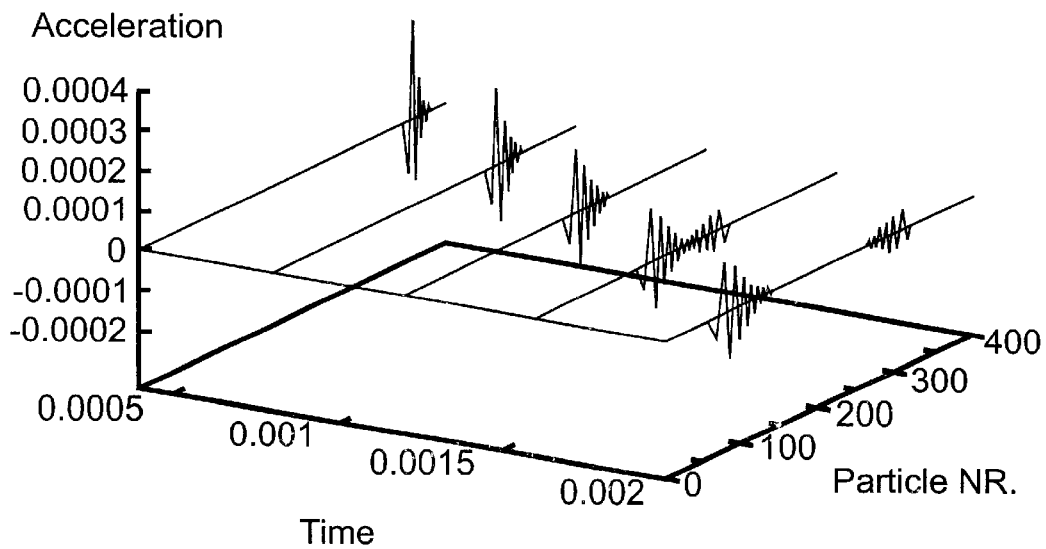
Figure 8B:
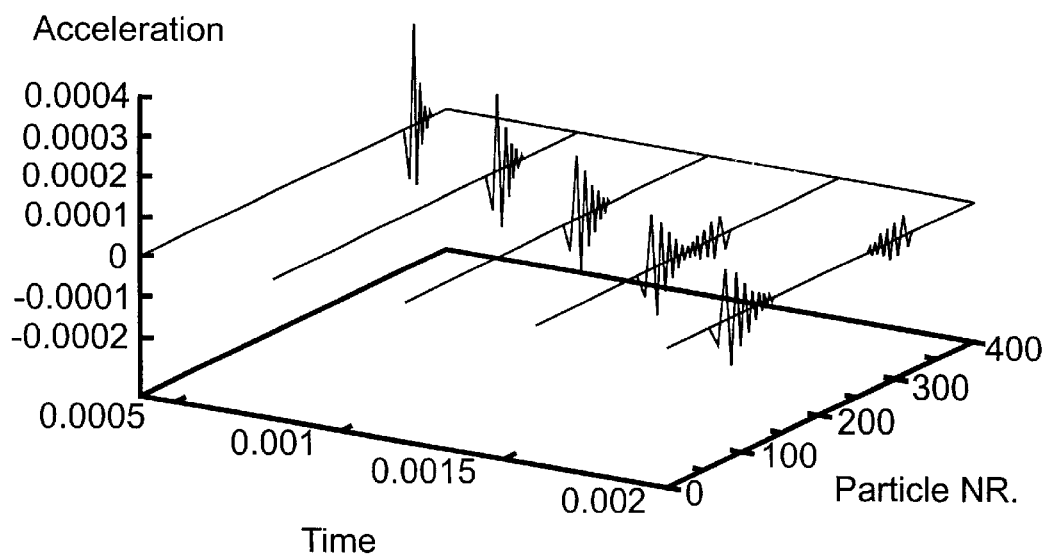

FIGS. 8a and 8b are graphs showing the kinetic energy of a pulse traveling in a one-dimensional granular system with an embedded impurity. In FIG. 8(a) the impurity possesses a density that is less than that of the grains that make up the host medium while in FIG. 8(b) the impurity possesses a density that is more than that of the host medium.

Figure 9A:
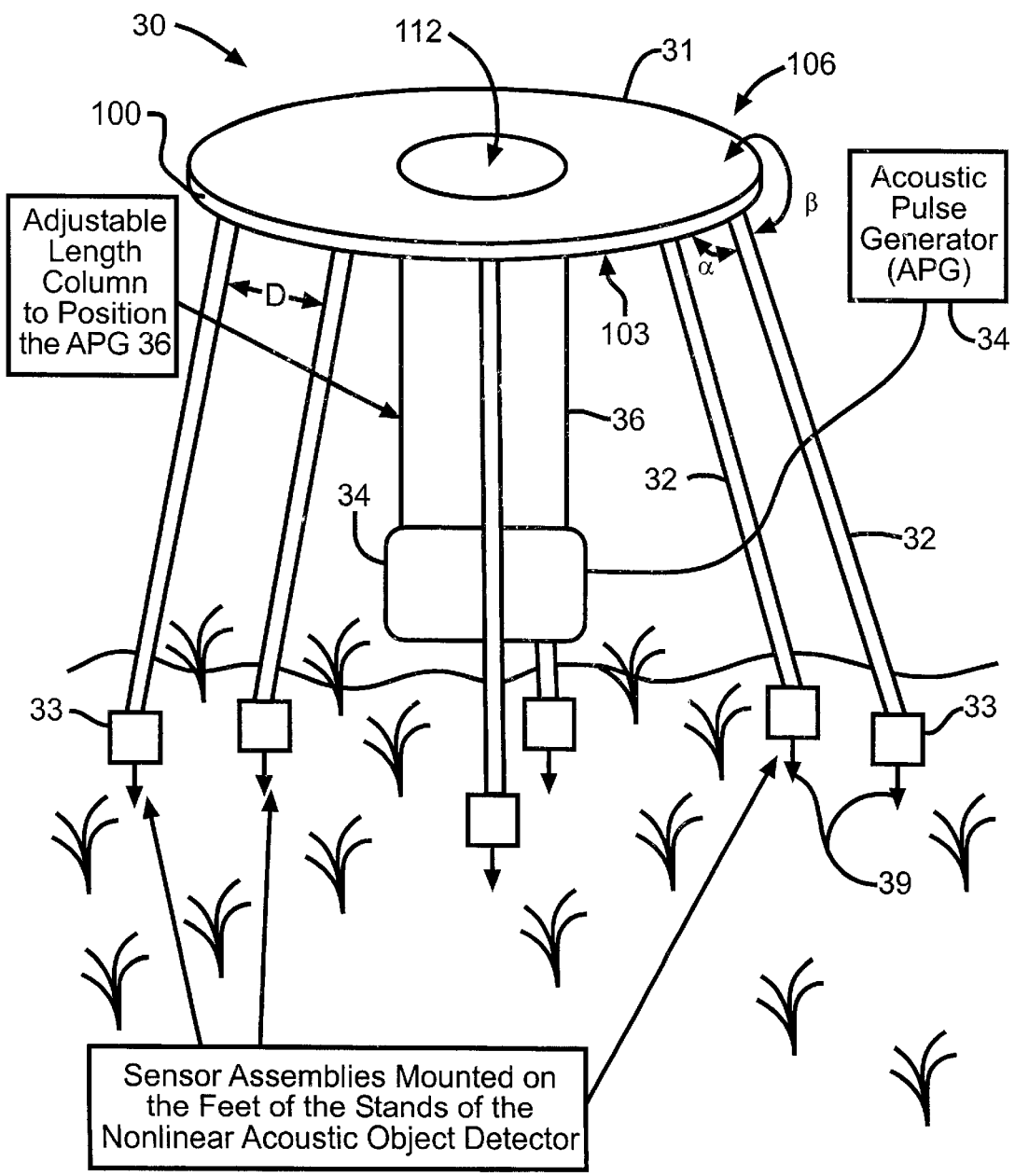

FIG. 9a is a schematic view of a land mine detector incorporating the invention.

FIG. 9b is a schematic view of the invention used by a control vehicle in a mine field.

Figure 9C:
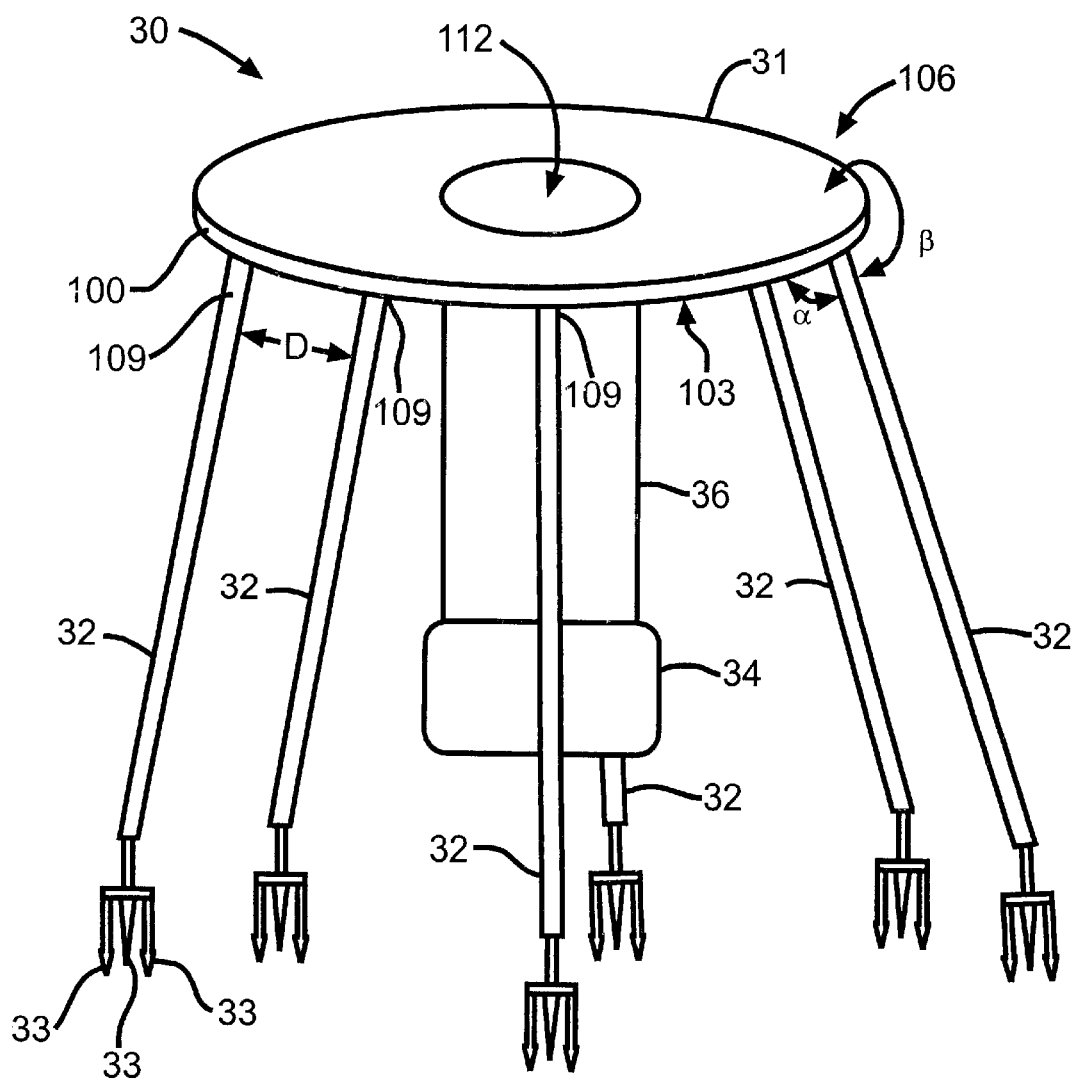

FIG. 9c is a schematic view of a land mine detector incorporating the invention.

Figure 10A:
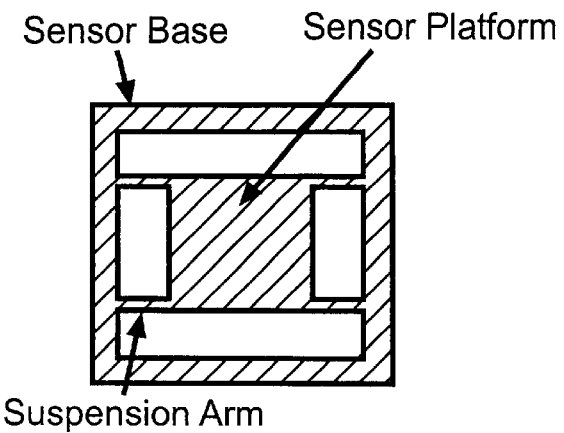
Figure 10B:
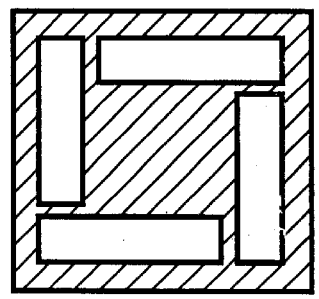
Figure 10C:
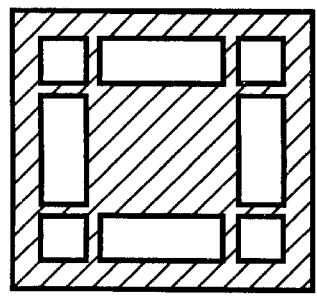
Figure 10D:
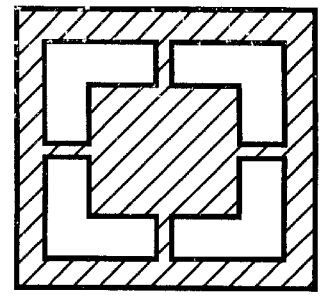
Figure 10E:
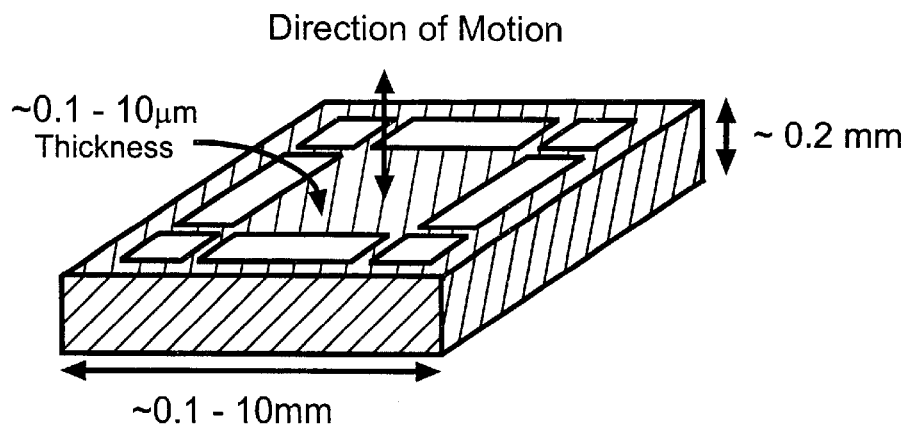

FIGS. 10a–10e show examples of platform configurations for microelectromechanical systems (MEMS) sensors that could be used in the detection system. FIG. 10e is a perspective view of a sensor.

Figure 11A:
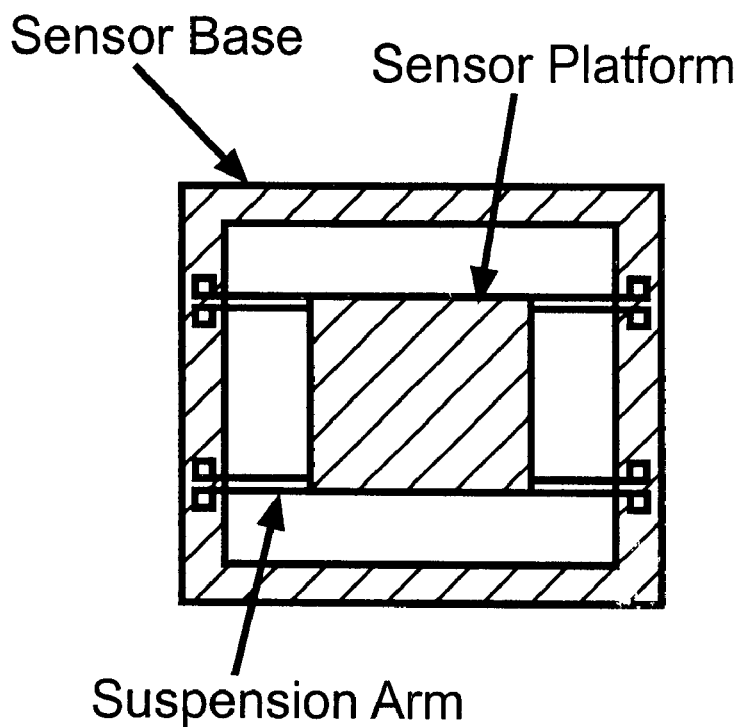
Figure 11B:
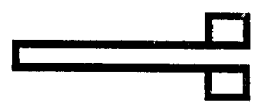

FIGS. 11a and 11b are respective plan and sectional views of a piezoresistive MEMS.

Figure 12:
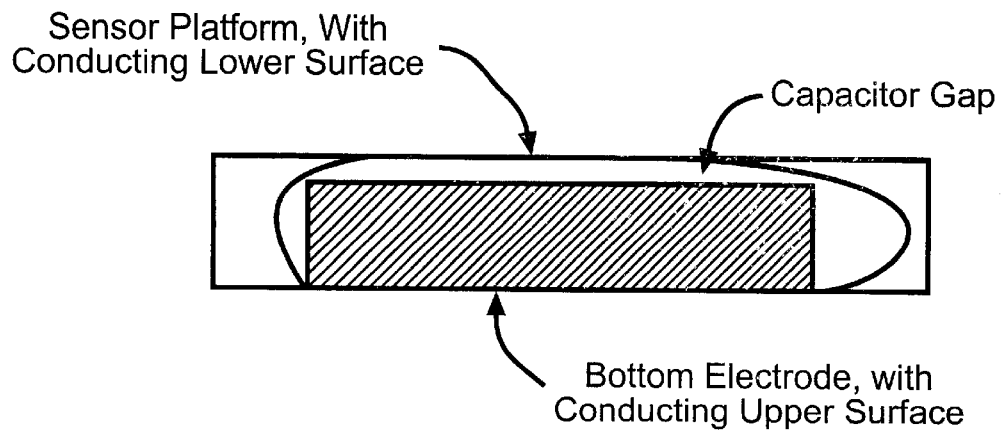

FIG. 12 is a sectional view of a capacitive MEMS.

Figure 13:
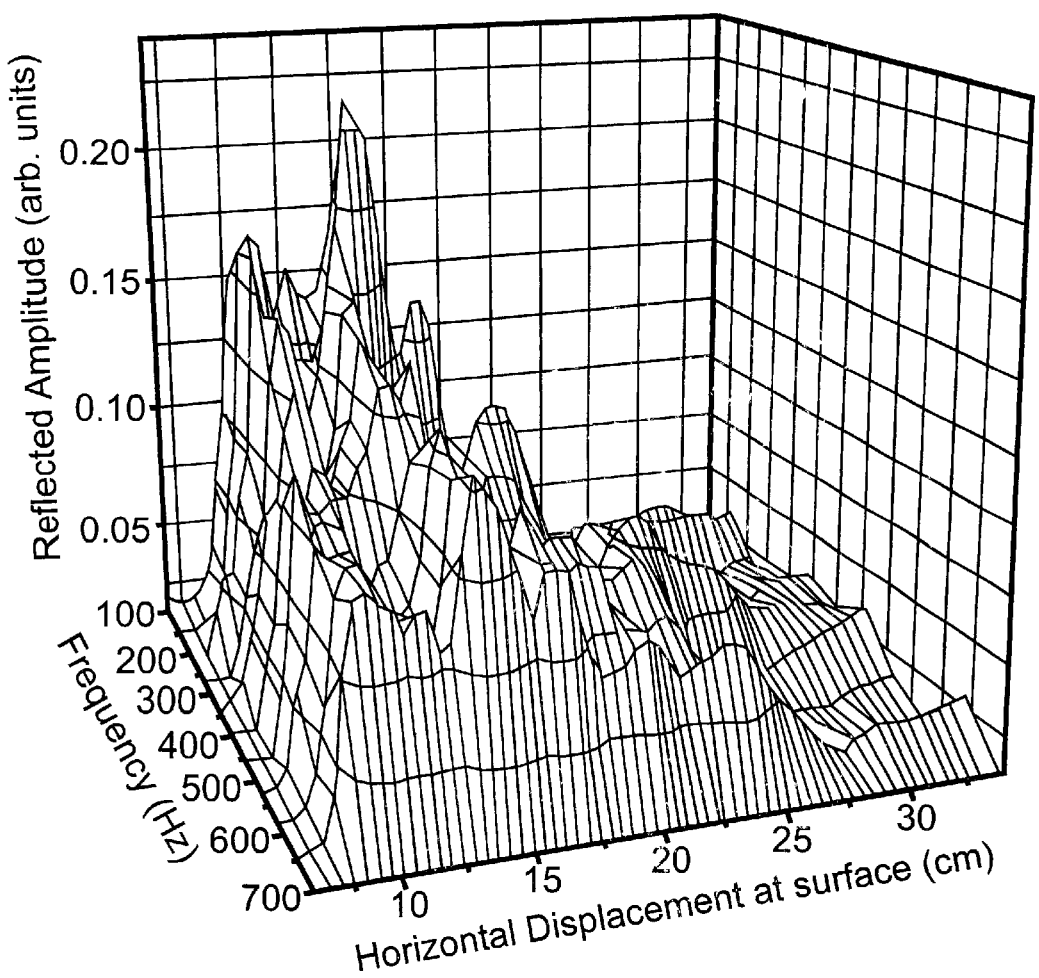

FIG. 13 is a three dimensional view of backscattered acoustic signals.

Figure 14:
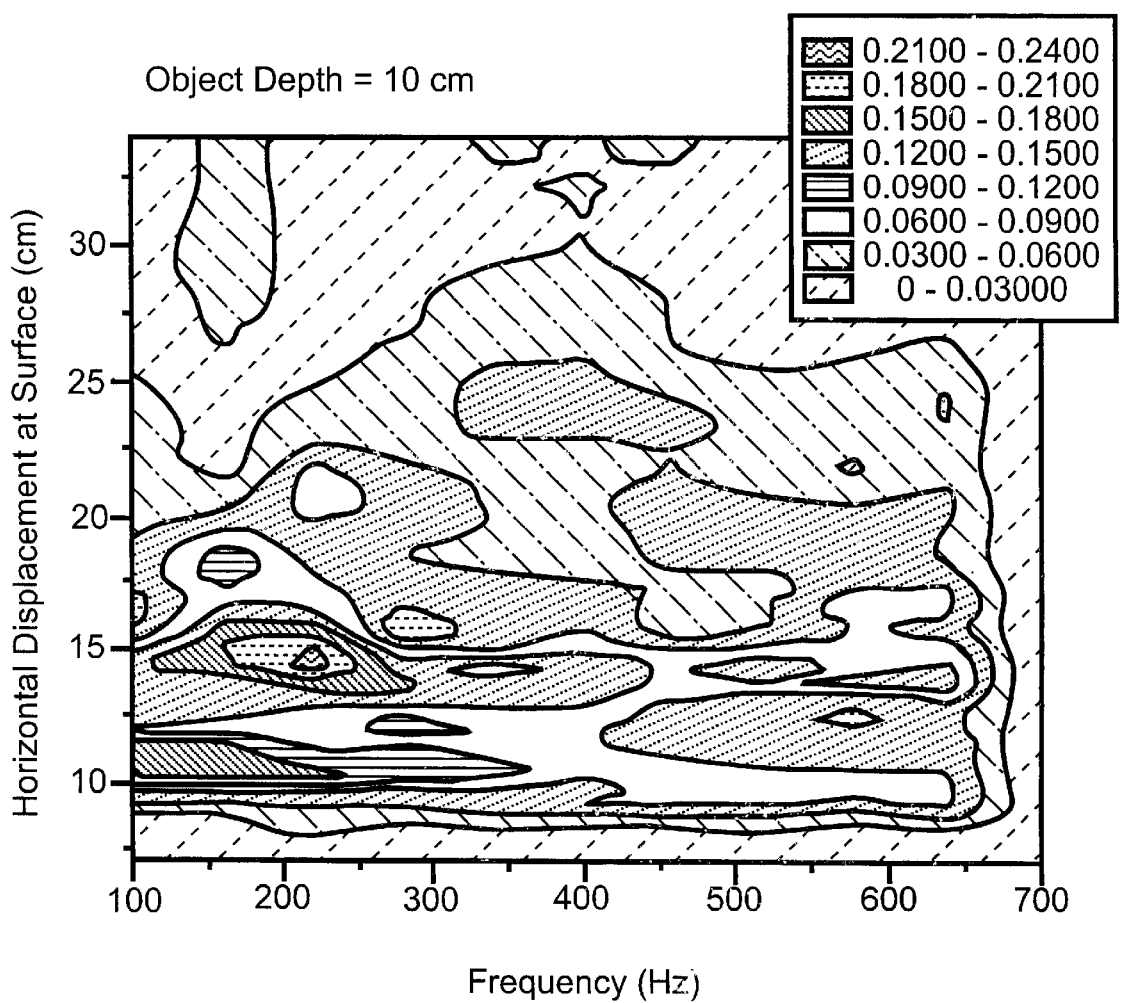

FIG. 14 is a contour plot of the data shown in FIG. 13.

Figure 15:
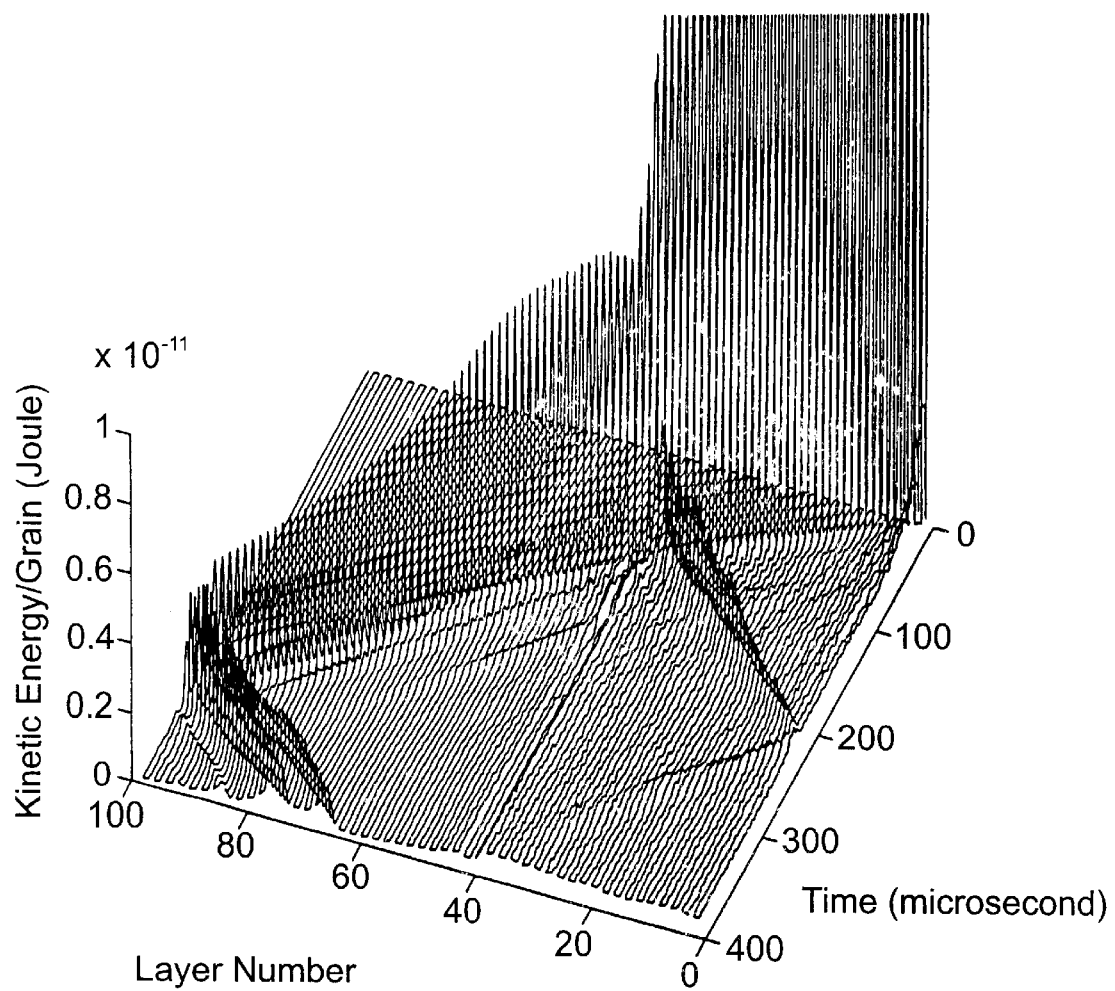

FIG. 15 shows the propagation of kinetic energy (measured in Joules and shown along the vertical axis) into a granular bed when an impulse is initiated at the surface of the granular bed.

DETAILED DESCRIPTION

The present invention recognizes that the amplitude of the traveling impulse decays exponentially in space and hence in time due to the net effects of restitutional losses and of randomness in grain sizes. The greater the degree of randomness and/or restitutional loss, the faster the exponential decay of the amplitude of the traveling pulse. The above formula for $\Phi_n(z)$ is approximately valid for the propagation of strongly non-linear acoustic impulses in granular media in three-dimensions and allows the computation of the amplitude, velocity, acceleration of the propagating pulse as well as the amplitude, velocity and acceleration associated with the motion of individual grains.

The present invention uses backscattering of the non-linear acoustic signals from a buried inclusion to locate and image the inclusion. The change in the density of the medium due to the presence of a buried inclusion results in a change in the amplitude of the pulse itself. The amplitude of the pulse depends upon the elastic constants that specify the granular contacts between the grains in the host medium and the inclusion. One can calculate the numerical values of the backscattered amplitude by solving the Newton's equations of motion for a three-dimensional granular bed with dissipation between the grains and with the effects of randomness of grain sizes and shapes using a particle dynamics computer code (Refs: O. Walton, *Mechanics of Materials,* Vol. 16, p.239 (1993) and S. Sen, M. Manciu and J. D. Wright, *Physical Review E,* Vol. 57, p.2386 (1998) and M. Manciu, S. Sen and A. J. Hurd, *Backscattering Of Non-Linear Acoustic Impulses From Buried Inclusions In Granular Beds,* Materials Research Society Symposium Proceeding, Vol. 627, pp. bb 3.5.1 to 3.5.6, eds. S. Sen and M. L. Hunt, (Materials Research Society, Pittsburgh, 2000)).

Therefore, one can calculate the detailed properties of backscattered pulses for given kinds of inclusions and for given distributions of inclusions. This knowledge is important for the interpretation of the signals received in the backscattered pulses in the applications of non-linear acoustic detection of buried objects in granular media such as in soil or some other granular assembly.

It is well known that in the presence of gravity or an applied external force field, the granular assembly suffers non-uniform loading, which varies with the depth or distance in the assembly as measured from the surface (Ref. R. S. Sinkovits and S. Sen, *Physical Review Letters,* Vol. 74, p.2686 (1995) and S. Sen and R. S. Sinkovits, *Physical Review E,* Vol. 54, p.6857 (1996)). For example, in a soil bed, the grains near the surface are less loaded (i.e., suffer less compression) than the grains which are located deep inside the bed (which suffer more compression). It is easier for a mechanical pulse or a continuous mechanical signal (as initiated by a speaker for example) to travel through grains in more intimate contact due to increased loading. Thus, the presence of a gravitational field increases both the velocity and the dispersion of the pulse with increasing depth. One is able to calculate and hence approximately characterize the velocity change and the dispersion of the pulse in a loaded granular assembly. The calculations are done by solving the dynamical equations for the grains with the conditions of loading incorporated into the calculations. The details of the calculations can be found in Ref. S. Sen, M. Manciu and J. D. Wright, *Physical Review E,* Vol. 57, p.2386 (1998) and M. Manciu, S. Sen and A. J. Hurd, *Backscattering Of Non-Linear Acoustic Impulses From Buried Inclusions In Granular Beds,* Materials Research Society Symposium Proceeding, Vol. 627, pp. bb 3.5.1 to 3.5.6, eds. S. Sen and M. L. Hunt, (Materials Research Society, Pittsburgh, 2000)).

Figure 1:
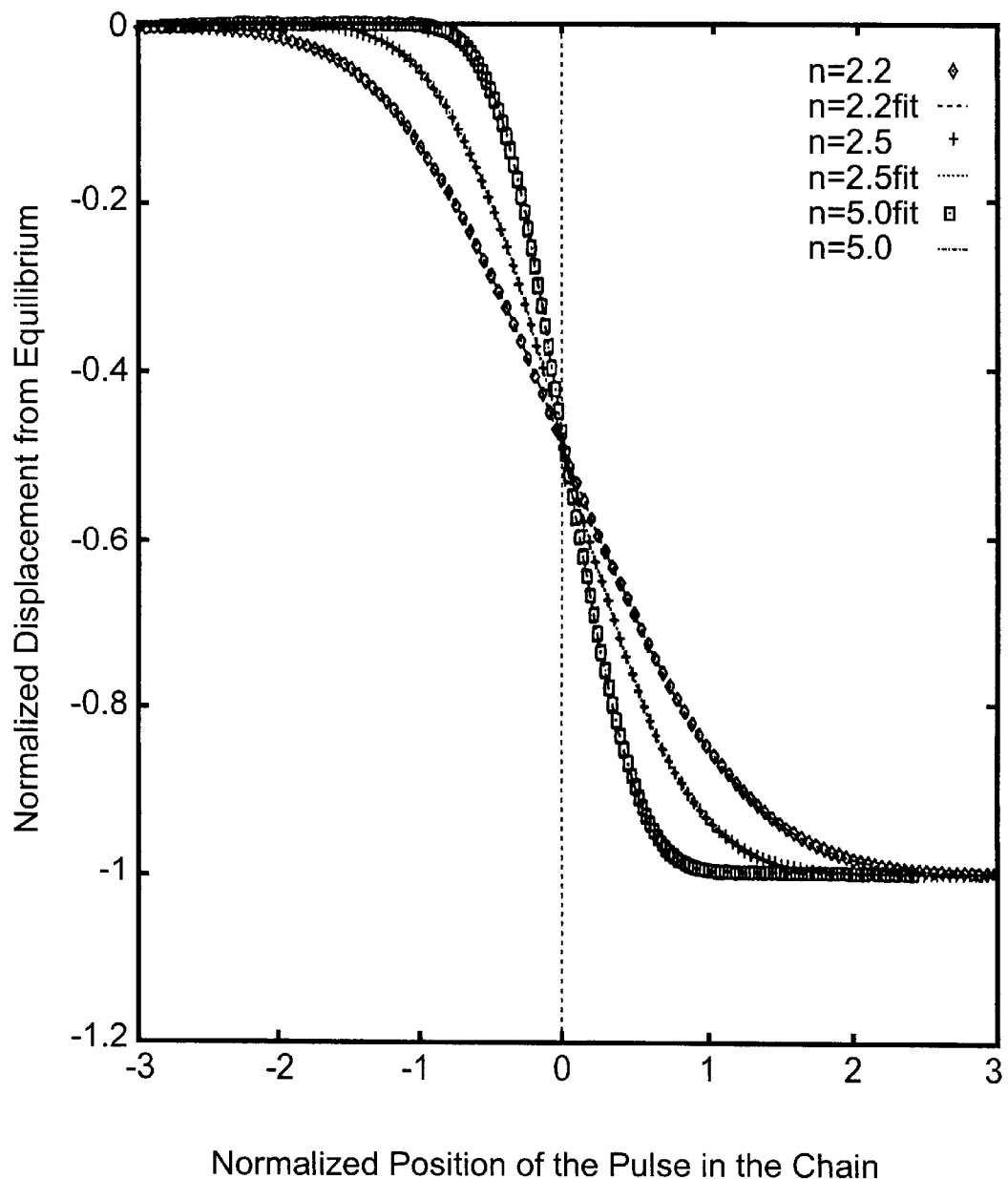
Figure 2:
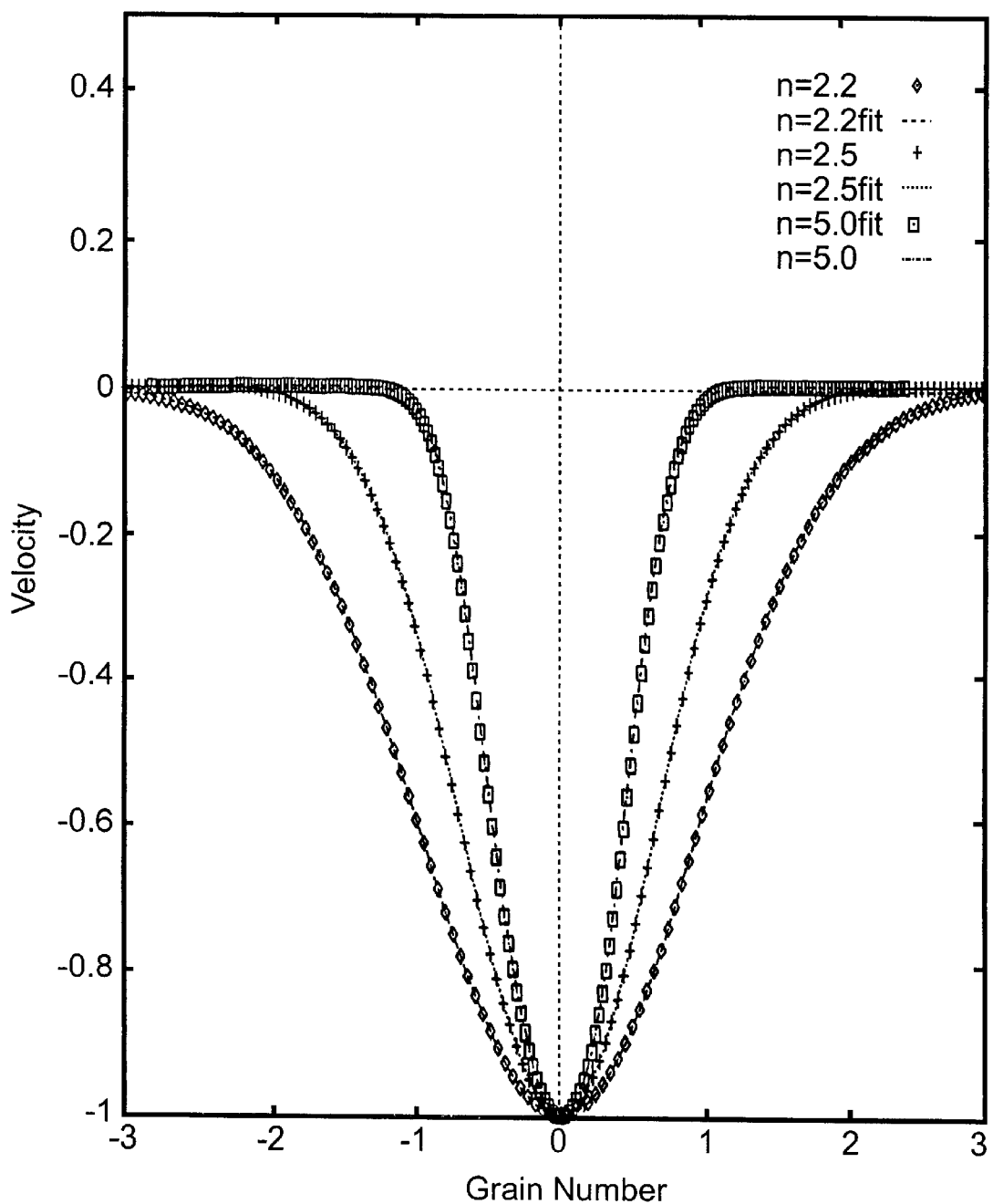
FIG. 2 is a graph showing velocity of grains as a function of their location in a chain of granular beads as a soliton passes through the chain, again calculated data and predictions based upon our solutions to the equations of motion for various values of n are shown.
Figure 3:
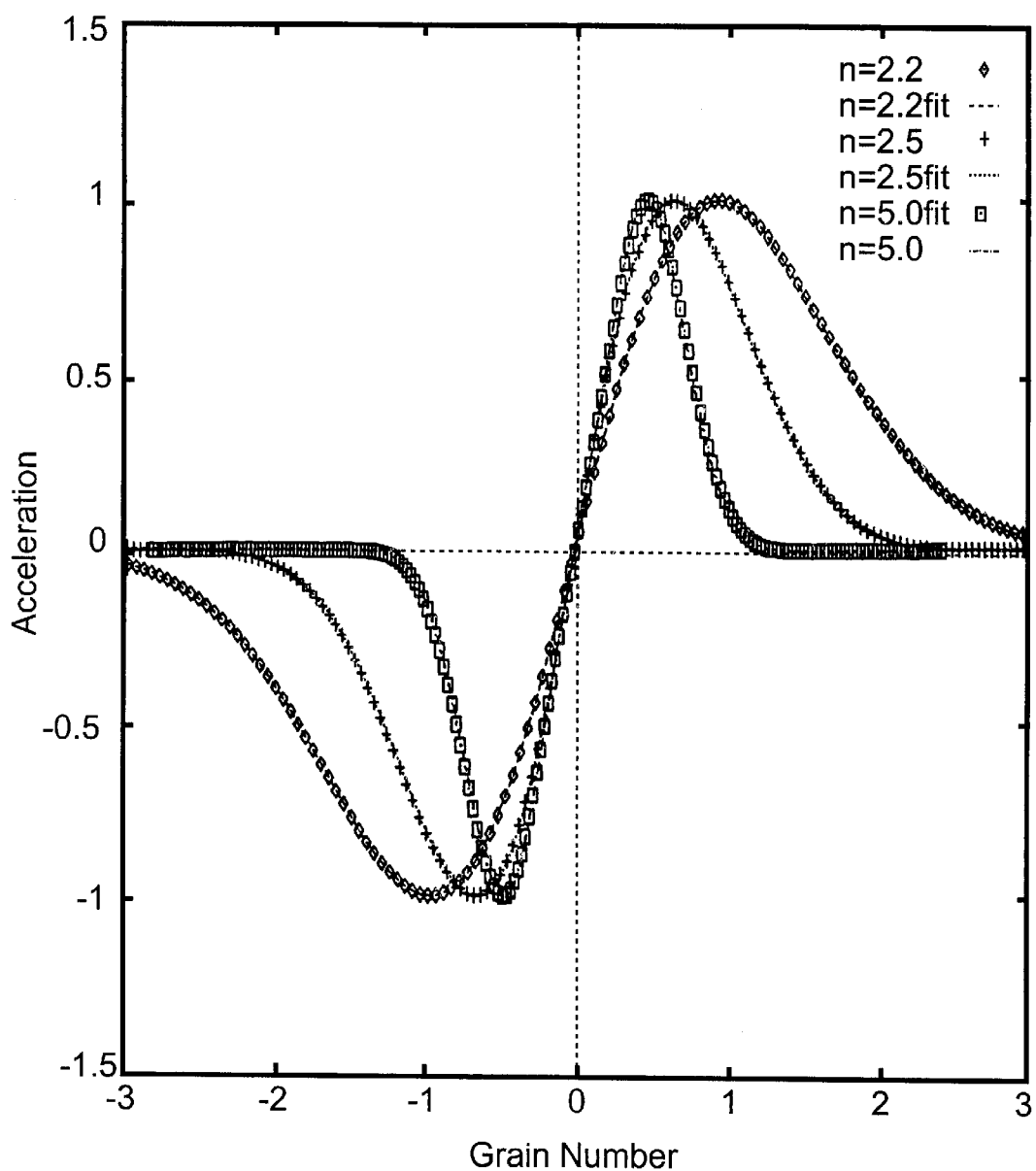
FIG. 3 is a graph showing calculated and predicted values of acceleration for various values of n as a function of grain location in a chain of granular beads as a soliton passes through the chain.

FIGS. 1–3 show, respectively, the displacement, velocity and acceleration for a chain of granular beads as a function of their location in response to a soliton pulse. The soliton decays with location. Note how in FIG. 4 the energy of the soliton pulse decreases with the grain number. The effect of variations in size and randomness is shown in FIG. 5. An example of the dispersion of the pulse with increasing gravitational field is given in FIG. 6. The nature of the change in the shape of the signal as it travels through a granular assembly that is subjected to an applied field is shown in FIG. 7.

We discovered that the nature of backscattering from a buried inclusion in a granular assembly in the presence. of an applied field is different from that in the absence of a field. FIG. 8 shows the kinetic energy of a pulse traveling in a one-dimensional granular system with an embedded impurity. In FIG. 8($a$), the impurity possesses a density that is less than that of the grains that make up the host medium, while in FIG. 8($b$), the impurity possesses a density that is more than that of the host medium. We have discovered that the leading edge of the backscattered pulse reveals information about the density of the buried object. Thus, when the reflected amplitude of the backscattered pulse is opposite to that of the initiated pulse, the buried object has a density that is greater than that of the medium, and when the reflected amplitude is in the same direction as that of the initiated pulse, the buried object possesses a density that is less than that of the medium (Ref. S. Sen, M. Manciu and J. D. Wright, *Physical Review E,* Vol. 57, p.2386 (1998)). For systems subjected to a gravitational field and hence to gravitational loading, the method works best when the pulse is initiated directly above the object.

Our invention provides a simple way to estimate the depth of a buried object in a granular assembly by estimating the nature of attenuation suffered by the amplitude of the impulse. The amplitude of the initial impulse A must be known. The amplitude of the reflected impulse A' must be determined by a suitable sensor device. Then, $$A'/A = \exp(-g(w,\rho)z),$$

from which statement the value of z, the depth of an inclusion, can be inferred.

The process of detecting buried inclusions in granular beds using continuous acoustic signals is different from the non-linear process. The continuous tone is used to detect buried objects at relatively shallow depths (e.g., typically less than 1 meter in soil). The continuous tone uses a frequency range of between 10 Hertz and 20,000 Hertz and preferably between 100 Hertz and 500 Hertz. At those frequencies the attenuation of acoustic signals is quite low in most granular assemblies including soil. It should be noted that different soil types have different frequency responses. Thus, it is important to characterize the frequency response of the soil or the granular assembly of interest before determining the frequency of the signal or signals that should be used for detecting a buried inclusion or many buried inclusions in that assembly. Also for frequencies of 20,000 Hz or less, a continuous wave signal can be viewed as a series of impulses.

FIGS. 9a, 9b and 9c show a detection system according to the present invention. The system shown in FIGS. 9a, 9b and 9c includes a land mine/inclusion. detector 30 capable of generating continuous wave acoustic signals at a desired frequency or frequencies and non-linear acoustic impulses. The acoustic detector 30 has an annular platform 31 supported by a plurality of legs 32 arranged around the outer edge of the platform 31 and extending at an angle to the surface 51 of a mine field 50. On the end of each leg is an acoustic sensor 33 described in more detail below. Each sensor 33 has a tip 39 that contacts the soil of the mine field 50. An acoustic pulse generator (APG) 34 extends from the center of the platform 31 toward the ground via a telescoping column 36. The diameter of the platform 31 is about half the diameter of the circle described by the circle connecting the tips 39 of the sensors 33. In a typical detector the APG 34 is about six inches in diameter, the platform 31 is about one. foot in diameter and the angle and length of the legs 32 results in an array of sensors 33 with a diameter of about two feet. Those skilled in the art will understand that other arrangements and arrays are possible. For example, the array may be rectangular, hexagonal, or any other suitable shape. The size of the array may also be larger or smaller than the disclosed embodiment.

Control and data signals are carried by a control and data line 37 that extends from the platform 31 to the control vehicle 12. The telescoping column 36 has one or more motors (not shown) for raising and lowering the APG 34 in response to control signals received from the control vehicle 12. Adjusting the height of the APG 34 improves the detection of a buried inclusion as well as images of the buried inclusion. In response to a control signal, the APG 34 will assume a controlled height above the mine field 50 and will emit a controlled acoustic signal. The controlled acoustic signal is either a soliton-like non-linear acoustic impulse or a continuous tone. The impulse signal is effective for detecting shallow and deep inclusions, and the continuous tone signal is effective for detecting shallow inclusions.

The platform 31 has an outer edge 100 that may be a closed curve shape, such as a circle. The platform 31 may be annular shaped. A plurality of legs 32 are joined to the platform 31, and at least one acoustic sensor 33 is joined to one of the legs 32. The acoustic sensors 33 may be joined to an end of the corresponding legs 33, distal from the platform 31.

The plurality of legs 32 may be joined to the platform proximate to the outer edge 100. The legs 32 may extend from the platform 31 in a manner such that a distance D between any two legs 32 increases with increasing distance from the platform 31. Each leg 32 forms a corresponding first angle α with a first major surface 103 of the platform 31, and a corresponding second angle β with a second major surface 106 of the platform 31. In one embodiment of the present invention, the first angles α and the second angles β are greater than 90 degrees.

The acoustic pulse generator 34 is joined to the platform 31. The acoustic pulse generator 34 may be positioned relative to the place where the legs 32 connect (the "connection location 109"), to the platform 31 such that the acoustic generator 34 is about the same distance from each connection location 109. The acoustic pulse generator 34 may be positioned approximately the same distance from each sensor 33.

As shown in FIG. 9c, a leg 32 may have more than one sensor 33 joined thereto, or as shown in FIG. 9a, there may be only one sensor 33 per leg 32. As shown in FIGS. 9a and 9c, the sensors 33 may be positioned approximately the same distance from a central location 112 corresponding to the platform 31. A sensor 33 may be located approximately equidistant from.the two nearest acoustic sensors 33.

The sensors 33 receive the backscattered signals from the buried inclusion and transmit those signals to the control vehicle 12. The received signals are sent to a computer that may have an analog-to-digital converter for converting the input analog signals to digital values. The computer also maps the signals from the sensors 33 and keeps track of the location of the detector 30 in the mine field 50.

Using an articulated arm 14, the control vehicle 12 scans the mine field 50 with the detector 30 by following a scan path 40. The computer records and stores the results of a scan at each location of the detector 30 in the mine field 50. In a manner well known in the art, the signals from the sensors 33 may be displayed in three-dimensional intensity plots and two-dimensional contour plots. The latter helps locate a point on the surface of the mine field 50 that corresponds to the location of an inclusion. The three dimensional plot indicates the depth of the inclusion. The data provided by the acoustic sensors 33 can be manipulated in a well-known manner to provide an image of the shape of the inclusion. The image may be displayed on a computer display unit.

The amplitude of the impulse from the APG 34 is gradually increased from low to high so as to ensure the system uses the lowest input pulse amplitude for acceptable backscattering data to reconstruct an image of the buried object from some computer screen. The APG 34 is moved on the ground to map images of buried inclusions. While it is always possible that the highest possible amplitudes used will lead to the best quality of information about any buried inclusion in the granular bed, high amplitudes may also activate the inclusion or inclusions. If the inclusion contains high explosives, such activation may be especially dangerous.

In the present invention, the APG 34 generates continuous acoustic signals of chosen frequency and amplitude or an acoustic impulse of fixed magnitude and across a chosen time period. The adjustable column 36 that connects the APG 34 to the platform 31 can be used to initiate the acoustic pulse away from or at the granular bed of interest.

The sensors 33 mounted at the ends of the legs 32 that support the apparatus will receive the backscattered acoustic pulses. More legs can be introduced if deemed necessary. The received signals may be transmitted by telemetry or by the control and data line 37 to a remote computer (not by itself a part of this invention). The computer 20, shown in control vehicle 12, processes the data using the scientific information presented above and a computer-generated image of the buried object or objects will be reconstructed using the information received. It is desirable to consider an apparatus that generates the non-linear acoustic pulses over a small region of space and to sample the backscattered signals in the region in which the pulses were initiated and in its neighborhood.

A computer-reconstructed image of the buried inclusion is accomplished as follows. Properties of the non-linear acoustic signal used for probing, the data concerning the displacement, velocity or acceleration of grains in the neighborhood of any given detector and the properties of the soil (for example, material constitution and porosity) are stored in a computer. The computer is programmed with a suitable computer algorithm for matching the stored data with an archived library of images of backscattering patterns and backscatterers. For example, prior to looking for land mines, tests are made of different types of land mines buried in different types of soil. Results of those tests are stored in the computer. The results of the field survey are depicted as (i) a recognizable object and object details, and (ii) an unrecognized object. The latter will require further probing with non-linear acoustic pulses of larger amplitude. The computer algorithm for generating such an image is with the skill of those knowledgeable in the field of computer imaging.

Experimental Realization of Non-linear Acoustic Probing

The present invention offers methods and devices for detecting and imaging buried objects in granular assemblies. For example, the present invention may be used to detect metal-poor land mines using non-linear acoustics, which may include solitons and soliton-like waves. The present invention may include microelectromechanical systems (MEMS) sensors 33. An acoustic impulse is imparted onto the surface of the granular medium by means of a shock pulse generator. A resulting shockwave is transmitted through the medium in the form of a soliton-like impulse. A soliton is a traveling wave bundle characterized by a complete or partial lack of attenuation in time and space. When this soliton-like impulse reaches the location of a buried object, it is scattered. Some acoustic energy contained in the soliton-like impulse is directly backscattered, thus reaching the surface of the granular bed as a reflected soliton-like pulse. Calculations have shown that the characteristics (amplitude, phase) of this soliton-like pulse contain information about the object off which it was scattered. The backscattered soliton-like pulse is detected at the surface of a granular bed, or for example the earth's surface, by the sensor 33, which may be selected from a number of currently available sensors, including for example, model #KP-135 PVDF manufactured by KTech Corporation located in Albuquerque, N. Mex. or a microelectromechanical systems (MEMS). sensor.

A MEMS sensor 33 can take the form of a cantilever of thickness between 0.1 and 10 micrometers and length between 10 micrometers and a few millimeters, or a planar membrane of lateral dimensions between 0.1 and 10 millimeters, with a thickness range similar to the cantilever. The sensor 33 dimensions are chosen to match the bandwidth of the backscattered energy of the soliton-like impulse, itself a function of the composition and density of the granular (in this example, soil) medium and of the buried object. It is anticipated that an array of MEMS sensors 33 may be employed, whose sensitivities span a range of frequency bands, so as to be capable of detection of buried objects under a variety of medium/object conditions. The present invention includes the use of structured MEMS sensors 33 as described below to detect backscattered non-linear acoustic impulses including soliton-like pulses, and thereby to detect and image buried objects such as nonmetallic land mines and municipal pipelines, among others.

The MEMS sensor 33 may comprise a thin dielectric platform whose mechanical motion is transduced to an output signal. Two or more suspension arms, which may be a cantilever beam or a rectangular plate, can hold the platform. The thickness of the platform may be between 0.1 and 10 micrometers. The lateral dimensions may be between 0.1 and 10 millimeters. When impacted by an acoustic impulse, the platform is caused to move (vibrate). The subsequent motion of the platform can be detected by capacitance, by placing a rigid metallic electrode in close proximity to the platform, itself having a metallic layer coating to act as a counter-electrode. The motion can also be detected via a resistance change in piezoresistive elements deposited on or embedded in the platform suspension arms or beam. Additionally, the platform motion can be detected optically with, for example, a laser light.beam reflected off the platform and directed at a light detector such as a photodiode. The non-linear acoustic impulse imparted on the sensor 33 contains frequency, amplitude and phase information about the object, from which it was scattered, which is supplied to a computer for analysis. The platform shapes discussed above are shown in FIGS. 10a–10c. Four platform configurations are shown, each designed to be sensitive to mechanical motion in a direction perpendicular to the page, as indicated in FIG. 10d. Each sensor configuration employs a number of suspension arms suspending a sensor platform with respect to a sensor base. In capacitive detection (FIG. 12), the bottom surface of the sensor platform is coated with a conducting material such as copper or gold, with access to this surface provided by coating the entire lower surface of the sensor 33 and its base. A fixed in place bottom electrode is placed beneath the sensor 33 such that a capacitor gap of approximately 0.01-mm to 0.1 mm is arranged as shown. A displacement of the flexible sensor platform results in a capacitance change, yielding the desired signal. Alternatively, piezoresistive elements can be deposited on or embedded in the dielectric sensor platform and its suspension arms, as shown in FIG. 11a. A displacement of the flexible sensor platform results in a change in the piezoresistance, yielding the desired signal. Alternatively, laser light can be directed at the sensor platform from above or below, with the reflected light directed toward a nearby stationary optical sensor, such as a photodiode. A displacement of the flexible sensor platform results in a change in light intensity, yielding the desired signal.

The MEMS sensor 33 may be made from a single crystal silicon, but can be made from any dielectric material, such as another elemental or compound semiconductor (GaAs), or a polymeric material such as polyimide. For the case of the laser diode detection, the material can be metallic as well.

Portions of the MEMS sensors 33 are described in co-pending U.S. patent application Ser. No. 09/026,260, of co-inventor Naughton, et al. That application describes a MEMS based cantilever sensor, which employs continuous-wave acoustic signals to detect buried objects. That disclosure is hereby incorporated by reference. The pending application does not discuss non-linear acoustics, impulse acoustics or solitons, and it refers strictly to a cantilever sensor, and not to other structured sensor configurations described herein.

As an example of the signal output expected from such a sensing device, we show in FIGS. 13 and 14 the capacitance change as a function of frequency and distance for back-scattered acoustic waves from an object buried 10 cm deep in sand. In this example, the sensor's horizontal displacement was changed in discrete steps along the sand surface. The response frequency of the sensor was scanned between 100 and 700 Hz, and the resulting amplitude of capacitance change was recorded. The buried object was known to be positioned at a horizontal displacement of 15 cm. A clear peak in recorded amplitude is seen in FIG. 13 near this displacement, for frequencies near 200 Hz.

FIG. 15 shows the propagation of kinetic energy (measured in Joules and shown along the vertical axis) into a granular bed when an impulse is initiated at the surface of the granular bed. The surface is defined as Layer Number 1, and the maximum depth of the bed is defined as Layer Number 100. The bed corresponding to FIG. 15 was 30 grains wide, 30 grains long and 100 grains deep. The travel time of the impulse was measured in microseconds. The granular bed was modeled as a system of polydisperse grains with random variation in grain radii of about 3% and with an average grain diameter of about 1 millimeter. Restitutional loss of the propagating impulse was assumed to be 0.99. The results depicted in FIG. 15 do not change significantly when slightly larger restitional loss is assumed, for example w=0.95.

The granular bed corresponding to FIG. 15 had a buried object placed in Layer Number 40. The buried object was approximately 10×10 grain diameters in size. The buried object backscattered part of the impulse, which subsequently traveled back to the surface after about 200 microseconds from the time the impulse was sent toward the granular bed. Part of the impulse went through the buried object, reached the bottom of the granular bed, and was reflected off the bottom wall of the container surrounding the granular bed. The reflected impulse is associated with the need to contain the granular bed in the laboratory, and would not be present in a non-laboratory setting, such as an actual mine field 50.

The backscattered pulse that reaches the surface can be received by a wide array of currently available sensors 33. As described above, the sensors 33 send signals corresponding to the received backscattered pulse, and those signals can be used to make an approximate image of the buried object, and can also be used to determine the depth, size and material corresponding to the buried object. After testing various buried objects and recording the reflected backscattered pulses, a database can be made. The database can be compared to received backscattered pulses in an actual mine field 50 to further enhance the effectiveness of the present invention.

Having thus described the preferred embodiment of the invention, those skilled in the art will appreciate that further modifications to that embodiment are included in the spirit and scope of the appended claims. Those skilled in the art will also understand that the invention can be used to detect many types of inclusions other than land mines. For example, the invention may detect tunnels that will image since they are substantially less dense than the surrounding soil. Still other applications include oil, gas and mineral exploration where the deposits of oil, gas and mineral are found in soil, such as sand. The sand or soil may be on land or underwater.

What is claimed is:

1. A detection system, comprising:
a platform having an outer edge;
a plurality of legs joined to the platform, each of the legs forming a first angle with a first major surface of the platform, and forming a second angle with a second major surface of the platform, the first angle and the second angle being greater than 90 degrees;
an acoustic sensor joined to one of the legs; and
an acoustic generator joined to the platform.

2. The detection system of claim 1, wherein the plurality of legs are joined to the platform proximate to the outer edge.

3. The detection system of claim 1, wherein the outer edge defines a closed curve shape.

4. The detection system of claim 3, wherein the closed curve shape is circular.

5. The detection system of claim 1, wherein the platform is annular shaped.

6. The detection system of claim 1, wherein the legs extend from the platform in a manner such that a distance between any two legs increases with increasing distance from the platform.

7. The detection system of claim 1, wherein the acoustic sensor is joined to an end of the leg distal from the platform.

8. The detection system of claim 1, wherein a first one of the plurality of legs joins the platform at a first connection location, and a second one of the plurality of legs joins the platform at a second connection location, and a third one of the plurality of legs joins the platform at a third connection location, and the acoustic generator is joined to the platform such that the acoustic generator is about the same distance from each connection location.

9. The detection system of claim 1, wherein the acoustic generator is joined to the platform by an extendable column.

10. The detection system of claim 9, wherein the extendable column is a telescoping column.

11. A detection system, comprising:
a platform;
a plurality of legs joined to the platform;
an acoustic generator joined to the platform; and
a plurality of acoustic sensors, each acoustic sensor being joined to a different one of the legs at locations that place each of the acoustic sensors approximately the same distance from the acoustic, generator.

12. The detection system of claim 11, wherein the acoustic sensors are located approximately the same distance from a central location of the platform.

13. The detection system of claim 11, wherein a first one of the acoustic sensors is approximately equidistant from two nearest acoustic sensors.

14. The detection system of claim 11, wherein any one of the acoustic sensors is approximately equidistant from two nearest acoustic sensors.

15. A detection system, comprising:
a platform;
a plurality of legs joined to the platform;
an acoustic generator joined to the platform; and
a plurality of acoustic sensors, each acoustic sensor being joined to one of the legs at locations that place each of the acoustic sensors approximately the same distance from the acoustic generator.

16. The detection system of claim 15, more than one acoustic sensor is joined to at least one of the legs.

* * * * *